United States Patent
Welt et al.

(10) Patent No.: US 8,567,236 B2
(45) Date of Patent: Oct. 29, 2013

(54) METHOD AND APPARATUS FOR MEASURING GAS TRANSMISSION RATE OF SEMI-BARRIER MATERIALS

(75) Inventors: Bruce Welt, Gainesville, FL (US); Ayman Abdellatief, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 381 days.

(21) Appl. No.: 12/335,230

(22) Filed: Dec. 15, 2008

(65) Prior Publication Data
US 2009/0158817 A1 Jun. 25, 2009

Related U.S. Application Data

(60) Provisional application No. 61/013,494, filed on Dec. 13, 2007.

(51) Int. Cl.
*G01N 15/08* (2006.01)

(52) U.S. Cl.
USPC .................................................. 73/38

(58) Field of Classification Search
USPC ................................................ 73/38, 866
See application file for complete search history.

(56) References Cited

U.S. PATENT DOCUMENTS

| 4,715,217 | A  | * | 12/1987 | Coyne et al. ................. 73/61.55 |
| 6,422,063 | B1 | * | 7/2002  | Anantheswaran et al. ....... 73/38 |
| 6,834,532 | B2 |   | 12/2004 | Izutsu et al. |
| 7,004,010 | B2 |   | 2/2006  | Larsen et al. |

OTHER PUBLICATIONS

Ocean Optics Inc. MultiFrequency Phase Fluorometer. Website page generated Oct. 2006 an accessed from archive.org. http://classic-web.archive.org/web/20061016010701/www.oceanoptics.com/Products/mfpf100.asp.*

* cited by examiner

*Primary Examiner* — Hezron E Williams
*Assistant Examiner* — Mark A Shabman
(74) *Attorney, Agent, or Firm* — Saliwanchik, Lloyd & Eisenschenk

(57) ABSTRACT

A method and apparatus is provided for measuring the oxygen transmission rate (OTR) of a material, such as a perforated film packaging material. The method and apparatus can use a fiber optic oxygen sensor that does not consume oxygen and does do not require any flowing gas during measurement of the OTR.

52 Claims, 4 Drawing Sheets

METHOD AND APPARATUS FOR MEASURING GAS TRANSMISSION RATE OF SEMI-BARRIER MATERIALS

CROSS-REFERENCE TO RELATED APPLICATION

The present application claims the benefit of U.S. Provisional Application Ser. No. 61/013,494, filed Dec. 13, 2007, which is hereby incorporated by reference herein in its entirety, including any figures, tables, or drawings.

BACKGROUND OF INVENTION

The shelf life of many food products is dependant on the oxygen transmission rate (OTR) of the material used to package the food. This is especially true during long-term storage. The presence of oxygen leads to many reactions that can decrease the shelf life of many foods. Microbial growth, oxidation of lipids causing rancidity, and senescence of fruits and vegetables all require oxygen to take place. Thus, it is important to the food industry that the OTR of packaging materials are consistent with the needs of products.

Attempts to predict transmission rates of gases through perforated films and other types of semi-barrier materials have been made. Emond et al. (1991) and Fonseca et al. (1996) used empirical models to describe diffusion of gases through perforated films. Also, Fishman et al. (1996) modeled transmission rates of gases using Fick's law of diffusion, while Hirata et al. used Graham's law of diffusion. Renault (1994) modeled diffusion of gas through perforated films with Maxwell Stefan's law. Ghosh and Anantheswaran (1998) determined that models based on Fick's law were in closest agreement with experimental data.

Oxygen transfer rate of perforated film depends on two mechanisms including permeation of oxygen through the base film and diffusion of oxygen through the perforations. Total flow through the film was described by Fishman et al. (1996) as:

$$F = JA + J_h A_h \quad (1)$$

where A is the total area of the film, J is the flux of oxygen through the film, $A_h$ is the total area of the holes, and $J_h$ is the flux of gas through a unit area of a hole.

Permeation of gas through film is given by:

$$J = \frac{-P(p_i - p_A)}{L} \quad (2)$$

where P is the permeability of the film, L is film thickness, $p_i$ is partial pressure of oxygen inside the package and $p_A$ is partial pressure of oxygen in the atmosphere surrounding the package.

Diffusion of oxygen through perforations should obey Fick's Law:

$$J_h = \frac{-D(p - p_A)}{L_h} \quad (3)$$

where D is the diffusion coefficient of gas in air through the perforation and $L_h$ is the diffusion path length. If the distance between perforations is much greater than the radius of the perforation, then $L_h$ can be approximated by the model employed by Meidner and Mansfield (1968) and Nobel (1974) for stomatal resistance.

$$L_h = L + R_h \quad (4)$$

where $R_h$ is the radius of the hole. Combining equations (1), (2), (3), and (4) yields $$F = (p_A - p)\left[\frac{AP}{L} + \frac{A_h D}{L + R_h}\right] \quad (5)$$

As an alternative to predicting an oxygen transmission rate (OTR), measurement of OTR of plastic packaging films and other semi-barrier materials can also be utilized for studying modified atmosphere packages (MAP). Typical existing methods to measure the OTR of a material involve passing an oxygen-containing gas and an oxygen-free gas on either side of the material. Oxygen moves through the material by permeation and is picked up by the oxygen-free gas, which flows to a sensor. In many cases, the sensor is a coulometric device. These methods do not work well with perforated films, though, because slight variations in gas flow rates or pressures on either side of the material can cause gas to flow through the perforations by convective mass-transfer. This can cause the measured OTR to be higher or lower than the actual OTR, depending on factors such as which side has the greater flow rate. To overcome these problems, the flow rates and pressures can be set and monitored very precisely, but this can be very expensive.

In addition, few commercially available films have sufficiently high oxygen transmission rates for packaging of respiring products. Many fruits and vegetables, such as strawberries and mangos have high respiration rates that make it difficult to supply sufficient oxygen through packaging films without perforations. Films with perforations having diameters on the order of 40 to 250 μm are generally referred to as microperforated films.

The use of perforated films in packaging materials is very common, especially with fresh-cut fruits and vegetables. However, design of packages using microperforated films has been difficult due to lack of methods capable of properly measuring OTR of films with perforations. In particular, the OTR of microperforated film depends on multiple factors including permeability of the film, perforation geometry, film thickness, and number of perforations in a given area of film. U.S. Pat. Nos. 6,422,063, 6,834,532, and 7,004,010 each describe methods for measuring the OTR of a perforated material. However, none of these methods is convenient, accurate, and cost-effective.

Difficulties measuring OTR of perforated films with traditional approaches is readily evident. Traditional methods include manometric, volume, coulometric, and concentration increase methods. For manometric and volume methods, a sample is typically mounted in a gas transmission cell to form a sealed semibarrier between two chambers. One chamber contains test gas at a specific high pressure, and the other chamber, which is at a lower pressure, receives the permeating gas. In the manometric method, the lower pressure chamber is evacuated and transmission of the gas through the film is indicated by an increase in pressure. In the volume method, the lower pressure chamber is maintained at atmospheric pressure and the gas transmission is indicated by a change in volume.

The coulometric method, an example of which is illustrated in FIG. 1, involves mounting a specimen as a sealed semi-barrier between two chambers at atmospheric pressure.

Referring to FIG. 1, instrumentation supplied by Mocon, Inc. (Minneapolis, Minn.) for implementing the coulometric approach is shown. FIG. 1 shows a procedure where oxygen would permeate from the right outer chamber test cell to left inner chamber test cell through the test film mounted between them. Here, the test film splits the test chamber into two halves. An oxygen containing gas (test gas) flows through the outer chamber test cell while an oxygen free gas (carrier gas) flows through the inner chamber test cell. The inner chamber is purged with a non-oxygen containing carrier gas, such as nitrogen, and the other chamber is purged with an oxygen containing test gas, which is typically ambient air (21% oxygen) or 100% oxygen. Oxygen permeates through the film into the carrier gas, which is then transported to a coulometric sensor. Oxygen is consumed in a process that generates an electric current proportional to the amount of oxygen flowing to the sensor in a given time period.

This coulometric system works well for film samples without perforations since slight variations of pressure on either side of the sample do not significantly alter measurements. However, with perforated films, variations in pressure can cause gas to flow freely from one side to the other, which directly affects oxygen measurements.

The concentration increase method, illustrated, for example, in FIG. 2, is an unsteady state method where the chamber is sealed with a semi-barrier and is initially purged with an oxygen free gas such as, for example, nitrogen. Oxygen diffuses through the barrier film and/or perforations, and the concentration of oxygen in the chamber is measured over time. The most common method used to measure the oxygen concentration is a gas chromatograph, which requires removal of gas samples from the test chamber, as illustrated by use of the syringe in FIG. 2. FIG. 2 shows a method for measuring OTR that requires headspace sampling over time (unsteady state measurement of headspace over time). Actual experiments often require removal of multiple samples from a single test specimen. Without perforations, each sampling changes headspace volume, which affects the measurement. With perforations, each sample draws new gas into the headspace so as to change gas compositions, thus affecting subsequent samples.

Accordingly, there exists a need in the art for a more convenient, accurate, and cost-effective method to measure the oxygen transmission rate of a material.

BRIEF SUMMARY

Embodiments of the present invention provide an accurate and low-cost method and apparatus to measure the oxygen transmission rate (OTR) of a material. Further embodiments can measure the transmission rates of other gases and/or vapors such as, but not limited to, carbon dioxide, water vapor, nitrogen, carbon monoxide, helium, hydrogen, ammonia, nitrogen oxides (NOx), sulfur oxides, hydrogen sulfide, hydrogen chloride, and aroma compounds. The method and device can be utilized to determine the OTR of a semi-barrier material. In specific embodiments, the method may be used to test the OTR on a perforated film packaging material. In further embodiments, the method and devices can be used to measure flow rates through non-perforated materials, such as non-perforated films.

Embodiments of the subject method pertain to a static method and do not utilize any flowing gases during measurement. The absence of flowing gases reduces, or prevents, measurement inaccuracies caused by streaming gases. Additionally, the absence of flowing gases reduces, or eliminates, the need for expensive hardware to precisely control pressures and gas flow rates. In certain embodiments of the invention, a fiber optic oxygen sensor is utilized to detect oxygen, so as to measure the OTR for a material. Specific embodiments utilize a fiber optic oxygen sensor that does not consume oxygen. In preferred embodiments, the fiber optic oxygen sensor is capable of sensing oxygen without using continuously flowing gases, consuming oxygen during measurement, or requiring removal of gas from a chamber for measurement. In further embodiments, sensors that consume or remove 5% or less of the oxygen, or other gas being measured, can be used. Fiber optic sensors with appropriate sensor substances can be used for a variety of substances. The subject invention can also utilize thermal conductivity detectors, and electronic nose sensors based on conductivity due to solubility in a substrate.

BRIEF DESCRIPTION OF DRAWINGS

In order that a more precise understanding of the above recited invention be obtained, a more particular description of the invention briefly described above will be rendered by reference to specific embodiments thereof that are illustrated in the appended drawings. Understanding that these drawings depict only typical embodiments of the invention and are not therefore to be considered as limiting in scope, the invention will be described and explained with additional specificity and detail through the use of the accompanying drawings in which.

DETAILED DISCLOSURE

Figure 1:
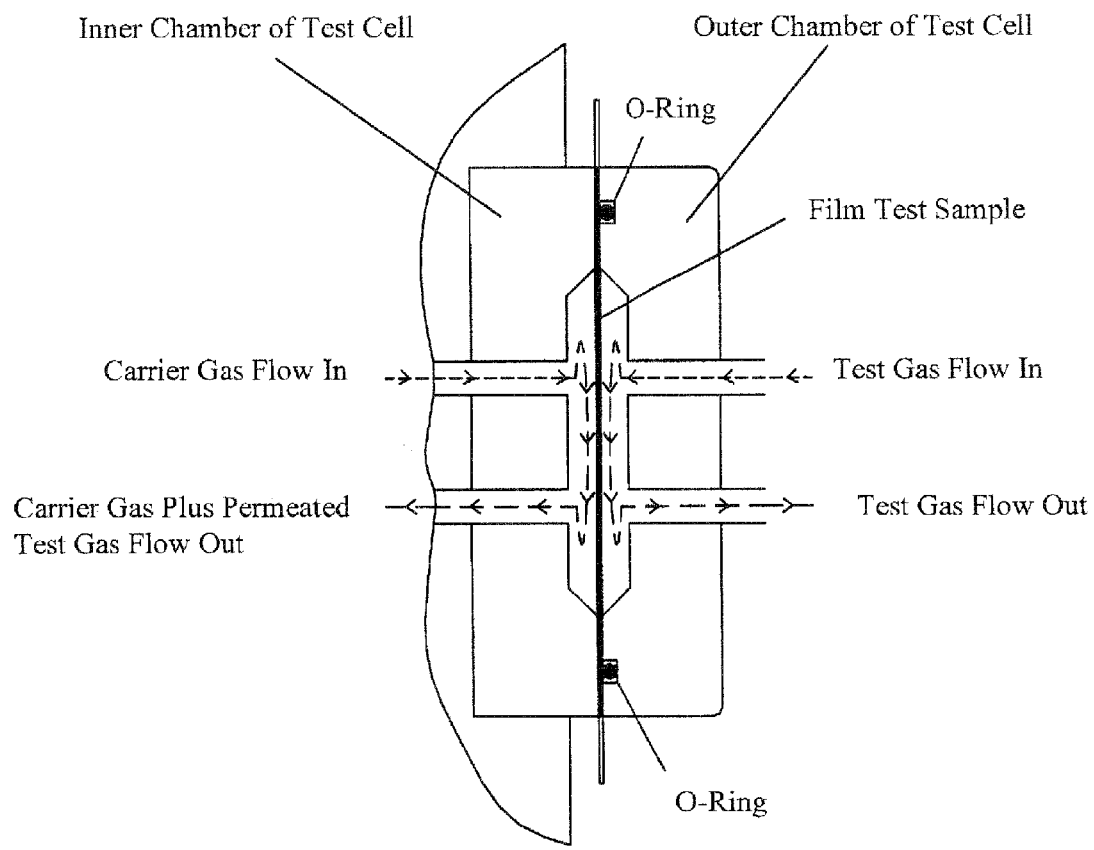
FIG. 1 shows a typical apparatus for measuring oxygen transmission rate (OTR) using a coulometric method.
Figure 2:
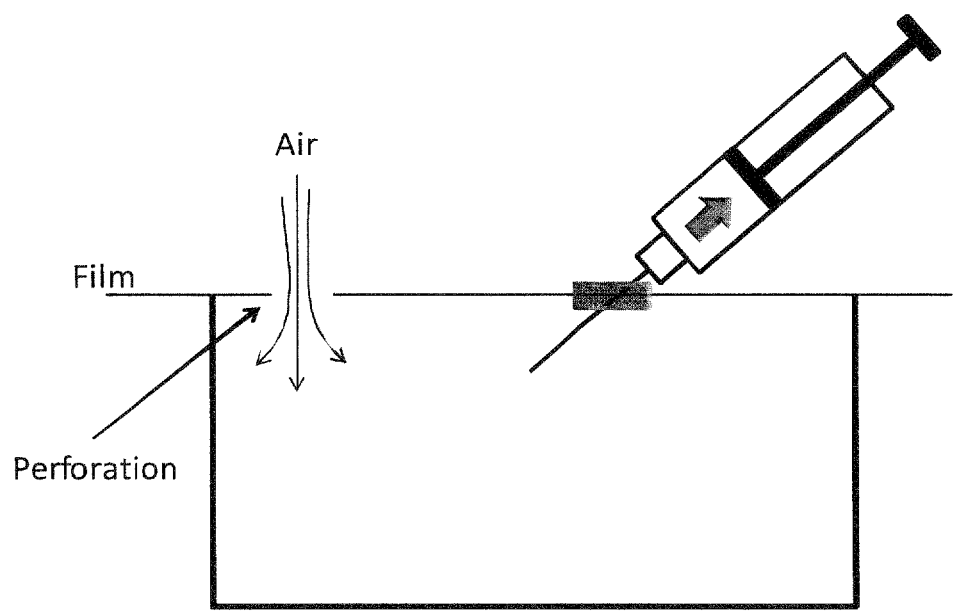
FIG. 2 shows an apparatus for measuring OTR, which requires headspace sampling over time (unsteady state measurement of headspace over time).

Embodiments of the present invention provide an accurate and cost-effective method and apparatus for measuring the oxygen transmission rate (OTR) of a material. Further embodiments can measure the transmission rates of other gases, vapors, and/or other airborne substances such as, but not limited to, carbon dioxide, water vapor, nitrogen, carbon monoxide, helium, hydrogen, ammonia, nitrogen oxides (NOx), sulfur oxides, hydrogen sulfide, hydrogen chloride, and aroma compounds. The particular advantage of the subject method is that it can be implemented with a variety of semi-barrier materials as a static method that does not require flowing or moving gases. In specific embodiments, the method is used on a perforated film packaging material to determine the OTR for the perforated film packaging material. In further embodiments, the method can be used to measure flow rates through non-perforated materials, such as non-perforated films.

The terms "semi-barrier" or "perforated film," "non-perforated film" and "film" as used in the subject invention are merely for literary convenience. These terms should not be construed as limiting in any way. It should be understood that the devices, apparatuses, methods, techniques and/or procedures of the subject invention could be utilized with any material through which gases, vapors, or other substances can permeate and be measured with the devices of the subject invention.

Embodiments of the subject method can use a fiber optic oxygen sensor that does not consume oxygen. The use of a fiber optic oxygen sensor that does not consume oxygen can lead to a more accurate measurement of the OTR of the material. Also, the subject methods and device can utilize any of a variety of sensors, including commercially available oxygen sensors, thus making it convenient to use and keeping the cost of the method and/or apparatus low. In further embodiments, sensors that consume or remove 5% or less of the oxygen, or other gas being measured, can be used. Fiber optic sensors with appropriate sensor substances can be used for compounds and substances. Thermal conductivity detectors, and electronic nose sensors based on conductivity due to solubility in a substrate can also be utilized with the disclosed methods and devices.

Embodiments of the method and apparatus in accordance with the present invention are particularly useful with perforated films, since no flowing gases are used. Furthermore, reducing, or eliminating, the use of flowing gases for the detection of oxygen that has passed through a material can reduce, or eliminate, the need for expensive equipment to precisely control pressures and flow rates of gases.

Embodiments of the subject method are more efficient, accurate, and cost-effective than currently existing OTR measurement methods. A specific embodiment of the subject method and apparatus for measuring the OTR of a semi-barrier material, such as a plastic packaging film, involves locating oxygen, or allowing oxygen to be provided, on one side of the barrier material/film and providing a fiber optic oxygen sensor on the other side of the material. Oxygen permeates through the barrier material or film and is detected by the fiber optic oxygen sensor, which can then produce a time-dependent signal to be analyzed. This method can work well with perforated and non-perforated film material because the measurements represent the concentration of oxygen that has permeated through the film material.

According to embodiments of the present invention, a fiber optic oxygen sensor that does not require continuously flowing gases, consume oxygen during measurement or require removal of gas from a chamber for measurement can be used in obtaining the OTR of a material.

A particular embodiment of the subject invention uses a fluorescence-based fiber optic sensor that is capable of continuously measuring gas within the test apparatus without removing or consuming gas and without a need for continuously flowing gases.

Sensors based on fluorophores are known in the art and are commercially available for use with embodiments of the present invention. In a fluorescence based fiber optic sensor, fluorophores can be suspended in a sol-gel complex and mounted at the tip of a fiber optic probe. One such fluorescence based fiber optic sensor is an oxygen probe available from Ocean Optics Inc. (Dunedin, Fla.), which uses a fluorescing ruthenium complex. For durability, probes may be mounted in rigid shafts, such as, for example, steel shafts of varying diameter in a manner that resembles hypodermic needles. In a specific embodiment, an 18 gauge probe, such as Model FOXY 18G by Ocean Optics Inc can be used. To operate this oxygen probe from Ocean Optics, a pulsed blue LED sends light, at 475 nm, onto an optical fiber. The optical fiber carries the light to the probe tip, which excites the fluorophore to cause an emission at ~600 nm.

Excitation energy from the light carried through the probe tip can also be transferred to oxygen molecules in non-radiative transfers. Therefore, the probe's exposure to oxygen decreases or quenches the fluorescence signal. For an understanding of this effect, see "Quenching of luminescence by oxygen" by H. Kautsky in Trans. Faraday Soc., 35, 216-219 (1939).

Fluorescent energy from the fluorophores can be collected by the probe and carried through the optical fiber to a spectrometer. The degree of fluorescence quenching directly relates to the frequency of collisions. This relationship can provide information regarding, for example, the concentration, pressure and/or temperature of the oxygen-containing media.

Advantageously, the use of a fluorescence quenching based sensor allows for measurement of oxygen concentration without consuming any oxygen. In contrast to embodiments of the present invention utilizing the fluorescence quenching based sensor, related art methods require removal of gas from the system or consumption of oxygen, which can directly affects the permeation measurement.

Embodiments of the subject invention provide a method for measuring OTR of a perforated or non-perforated film, or other semi-barrier material, using a modified concentration increase method. The concentration increase method involves initially purging a chamber sealed with a semi-barrier with an oxygen free gas, such as nitrogen. Oxygen tends to diffuse through the semi-barrier. The concentration of oxygen that has diffused into the chamber through the semi-barrier can be measured over time. In accordance with embodiments of the present invention, the measurement of the oxygen concentration does not consume the sensor, the sensor does not consume any gases involved in the measurement, the apparatus does not require the use or consumption of constantly flowing gasses, and does not create or rely upon pressure differentials.

Figure 3A:
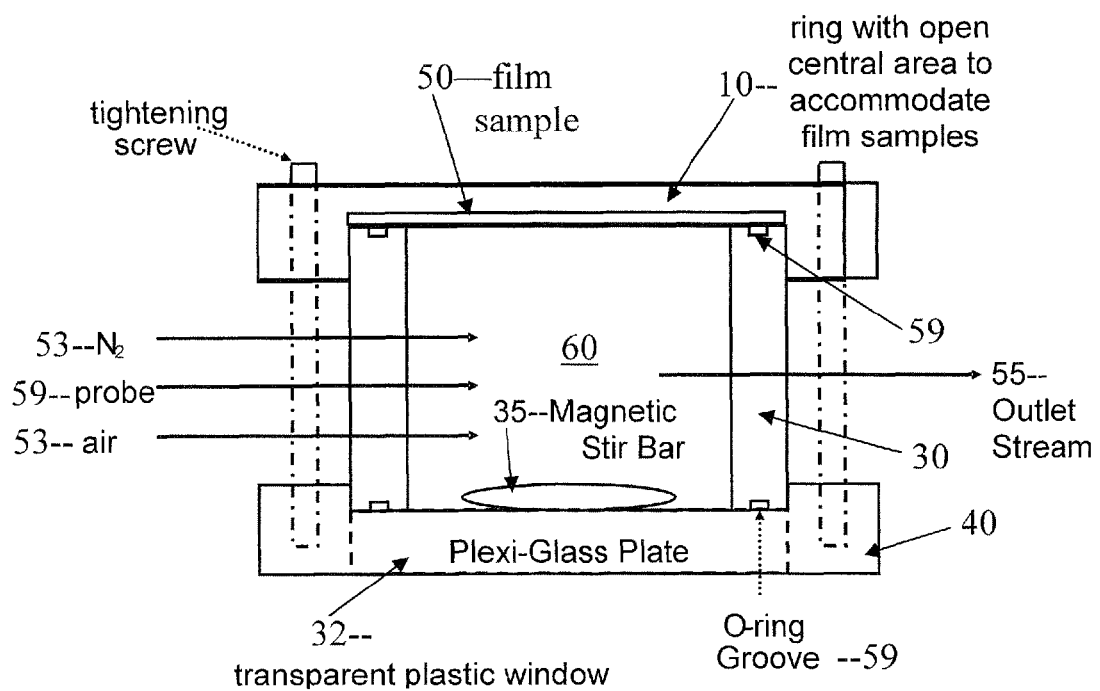
FIG. 3A shows a schematic profile of an OTR chamber according to an embodiment of the present invention.
Figure 3B:
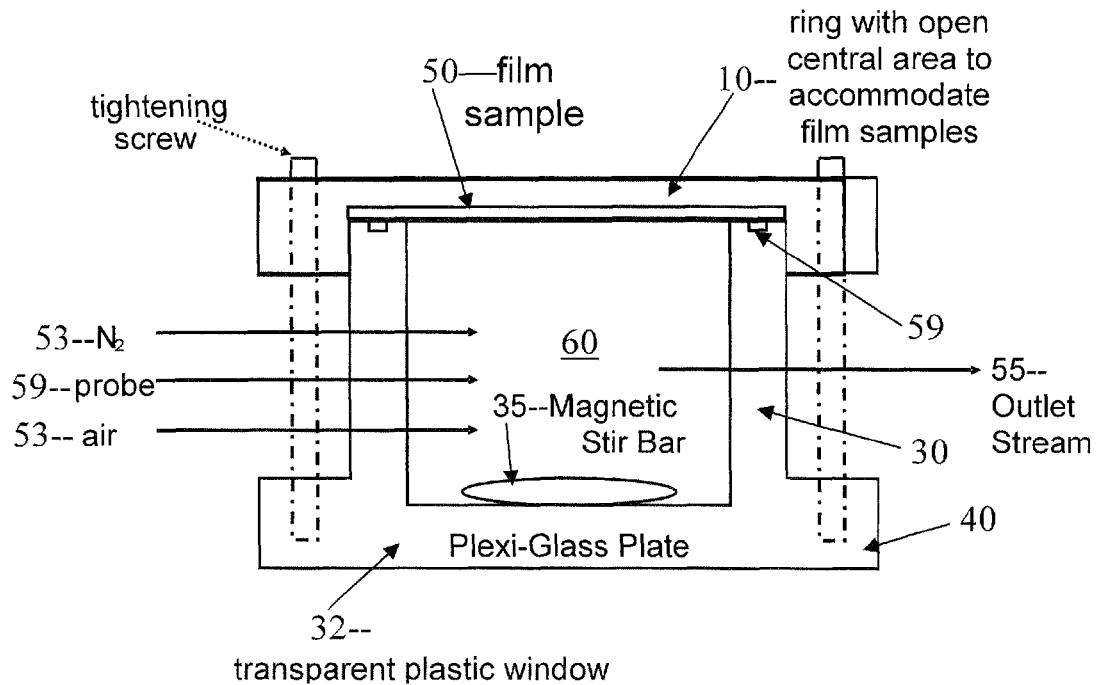
FIG. 3B shows a schematic profile of an alternative embodiment of an OTR chamber according to an embodiment of the present invention.

FIG. 3A shows a cross-section of a schematic profile of an embodiment of an apparatus for measuring OTR according to the present invention. Referring to FIG. 3, an OTR apparatus is, in general, a chamber having a sealable hollow interior. The chamber can be constructed in a multitude of variations known to those with skill in the art. In one embodiment, the chamber incorporates a container with a sealable lid, where at least a portion of the lid can hold a portion of a sample of the semi-barrier material. In particular embodiment, the sealable chamber can include a top section 10, a middle section 30, and a bottom section 40 that can be sealably attached. The top section 10 accommodates a film sample 50, which acts as the semi-barrier under test. The film sample can be a perforated film. The bottom section 40 can provide a lower barrier for the chamber 60 formed by the top 10, middle 30, and bottom section 40. In one embodiment, the bottom section is a separate component that can be brought into sealable contact with the middle section. The chamber can be sealed using o-rings that can fit into an o-ring groove and tightening screws that bring the top section towards the bottom section. In an alternative embodiment, shown in FIG. 3B, the bottom section and middle section are a single piece rather than separate components. In this embodiment, the bottom and middle sections can form a single unit with a hollow interior open at one end. The open end can be sealably connected to the top section to form a sealed hollow chamber.

In a further embodiment, the middle section can include one or more inlet ports 53 for introducing into the chamber interior a non-testing substance or a substance that does not affect the probe, and one or more outlet ports 55 for flushing the non-testing substance from the chamber 50. It can also include a sensor port 59 for mounting a probe, such as a fiber optic oxygen probe. In the embodiment shown in FIGS. 3A-3B, four ports are used, two inlet ports 53, one each for flushing the chamber with nitrogen and flushing the chamber with compressed air, a sensor port 59 for mounting a fiber optic oxygen probe within the chamber, and a gas outlet port 55 for venting the chamber 60. In alternative embodiments, the one more inlet and outlet ports can be located within other areas of the chamber, such as the bottom section or within the top or lid portion of the chamber. A person with skill in the art would be able to determine the appropriate location for the ports depending upon the configuration of the chamber components. Such variations in the chamber configuration and location of the ports are considered to be within the scope and purview of the subject invention.

The chamber can be initially purged of oxygen by using the nitrogen or compressed air port to flush the chamber. Then, as oxygen diffuses through a film sample, the fiber optic oxygen probe can be used to measure the concentration of oxygen in the chamber over time.

Tests were performed using an experimental set-up for an apparatus for measuring OTR according to an embodiment of the present invention. For this embodiment, the three sections (top 10, middle 30, and bottom 40) are fabricated from magnesium metal. However, alternative embodiments will utilize materials appropriate for the substances being tested with the methods and devices of the subject invention. A person with skill in the art would be able to determine any of a variety of materials suitable for the components of the subject invention and such variations are considered to be within the scope of the subject invention. In this embodiment, the bottom section incorporates a transparent plastic window or other non-magnetic material 32 in order to allow for a magnetic stir bar 35 within the test chamber. In an alternative embodiment, a single- or multi-blade fan can be positioned within the chamber interior to agitate the air or other substances within the interior. Alternative embodiments known to those with skill in the art, for allowing the substances permeating into the chamber to be well stirred or otherwise agitated could also be utilized with embodiments of the subject invention.

In this specific embodiment being tested, the height of the middle section is approximately 5.0 cm and is a hollow cylinder with four ports for flushing with nitrogen and compressed air, mounting the fiber optic oxygen probe, and to provide for a gas outlet valve. The middle section also accommodates o-rings for gas tight seals with the top and bottom sections. The top section is formed as a ring with an open area of approximately 50 cm² to accommodate film samples. It will be understood by those with skill in the art that the shape and dimensions of the middle section, as well as the top and bottom sections, can vary depending upon numerous factors. Such variations in size, shape and dimension of the components described herein, in so far as they do not detract from the teachings herein, are contemplated to be within the scope of this invention.

Films having hole diameters of 100.13 μm, 153.39 μm, 204.89 μm, and 248.95 μm were provided for an experimental set-up. Oxygen partial pressure in the chamber is recorded every 10 seconds using the average of four measurements with the fiber optic oxygen sensing system. Measurements are made at 15° C., 23° C., and 30° C. inside a computer-controlled environmental chamber. From the change in oxygen partial pressure over time, OTR of holes can be determined with the following Fick's law based equation for a well-stirred volume provided by J. P. Edmond in "Mathematical modeling of gas concentration profiles in perforation-generated modified atmosphere bulk packaging." (Ph.D. Thesis, University of Florida 1992).

Movement of oxygen through the film and orifice can be modeled using as follows $$\frac{dn_{O_2}}{dt} = \frac{\overline{P}_{O_2} A}{l} \left( p_{O_2}^{ambient} - p_{O_2}^t \right) \quad (1)$$

Figure 4:
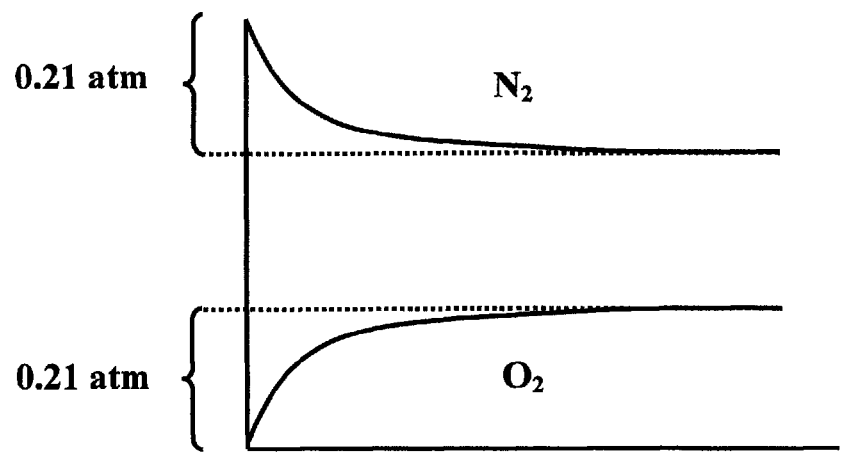
FIG. 4 illustrates the diffusion of oxygen and nitrogen under similar driving forces ranging from 0.0 to 0.21 atm.

For the case of perforated films, diffusion of oxygen and nitrogen experience similar driving forces ranging from 0.21 to 0, as seen in FIG. 4. Therefore, for perforated films, gas transfer rates of oxygen and nitrogen are similar.

$$\frac{dn_{O_2}}{dt} = \frac{dn_{N_2}}{dn_{O_2}} \quad (2)$$

For a rigid test apparatus with a perforated film mounted, volume and pressure are constant. Therefore, oxygen partial pressure can be related to moles of oxygen via $$p_{O_2} = \frac{n_{O_2} RT}{V_{total}} \quad (3)$$

Substituting Equation 3 into Equation 1 and using the ideal gas law to convert the units for the permeability coefficient from moles to ccO2 provides $$\frac{dp_{O_2}}{dt} = \frac{RT}{V_{total}} \cdot \frac{\overline{P}_{O_2} A}{l} \left( p_{O_2}^{ambient} - p_{O_2}^t \right) \quad (4)$$

Integrating Equation 4 provides $$\ln\left[\frac{p_{O_2}^{ambient} - p_{O_2}^t}{p_{O_2}^{ambient} - p_{O_2}^0}\right] = \frac{-RT}{V_{total}} \cdot \frac{\overline{P}_{O_2} A}{l} \cdot t \quad (5)$$

Taking the value of the slope of a plot of $$\ln\left[\frac{p_{O_2}^{ambient} - p_{O_2}^t}{p_{O_2}^{ambient} - p_{O_2}^0}\right]$$

versus t and solving for permeance, $$\frac{\overline{P}_{O_2}}{l},$$

and converting units, yields $$\frac{\overline{P}_{O_2}}{l} = \frac{|\text{Slope}| V_{total}}{A} \quad (6)$$

$$OTR = \frac{\overline{P}_{O_2}}{l} \cdot \left( p_{O_2}^{Air} - p_{O_2}^t \right) \quad (7)$$

Since Δp changes throughout the unsteady state experiment, the result is a plot that provides OTR as an asymptote to Δp. During the experiment, OTR is greatest when Δp is greatest at the beginning of the experiment and tends to zero as gas in the vessel approaches that of air. This plot can then be used to design a package where some desired oxygen level is desired in the package.

Figure 5:
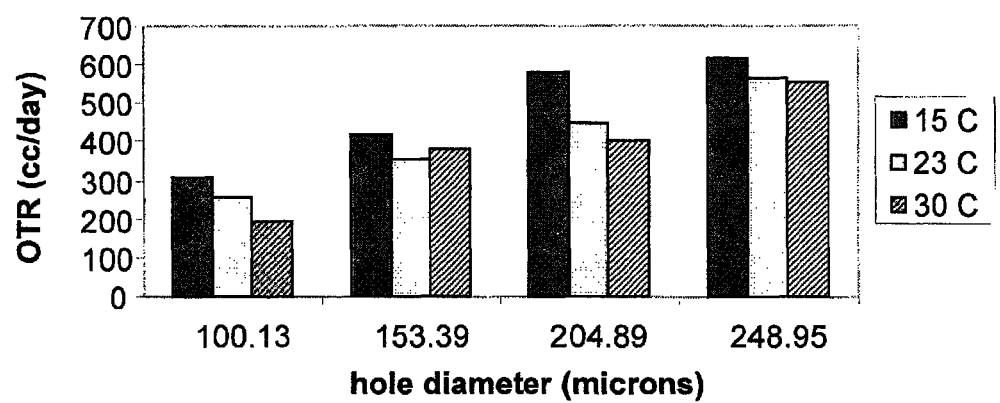
FIG. 5 shows the OTR of holes at different temperatures.

FIG. 5 shows OTR data for the tested holes at temperatures of 15° C., 23° C., and 30° C., and shows that the apparatus is capable of providing consistent and reliable measurements. Additional, FIG. 5 illustrates a tendency for OTR to decrease with increasing temperature, despite the fact that gas diffusion coefficients are generally known to increase with temperature. It is likely that reduced gas density at higher temperatures may offset increases in gas diffusion coefficients. However, for most modified atmosphere packaging applications, temperatures tend to be low and temperature variations are much less pronounced, which may reduce the potential impact of this observed trend.

Accordingly, an apparatus and method for measuring OTR of perforated thin films according to an embodiment of the present invention is capable of providing stable and repeatable measurements.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A device for measuring the transmission rate of a substance through a sample, comprising:
    a chamber having one or more walls that define an interior and an exterior, wherein the one or more walls have an aperture therethrough such that the interior communicates with the exterior through the aperture;
    a sample holder, wherein the sample holder positions a sample proximate the aperture such that the exterior and the interior are separated by the sample; and
    a probe, wherein at least a portion of the probe is in contact with the interior such that the probe can detect a substance in the interior, wherein the probe does not consume the substance during detection.

2. The device according to claim 1, wherein the probe comprises a fluorophore, wherein the fluorophore is in contact with the interior.

3. The device according to claim 1, further comprising:
    an inlet port for passing a purge gas or mixture from the exterior to the interior; and
    an outlet port for allowing gasses to pass from the interior to the exterior, such that when the purge gas or mixture is inputted through the inlet port, gasses in the interior are purged from the interior to the exterior through the outlet port.

4. The device according to claim 3, wherein the purge gas or mixture is a purge gas.

5. The device according to claim 4, wherein the purge gas is nitrogen.

6. The device according to claim 1, wherein the sample is perforated.

7. The device according to claim 6, wherein the sample comprises a permeable material.

8. The device according to claim 6, wherein the sample comprises a non-permeable material.

9. The device according to claim 1, wherein the sample is non-perforated.

10. The device according to claim 1, wherein the sample comprises a permeable material.

11. The device according to claim 1, wherein the sample comprises a non-permeable material.

12. The device according to claim 1, wherein the substance is oxygen, wherein the probe comprises an oxygen sensor.

13. The device according to claim 12, further comprising a port for insertion of the oxygen sensor into the interior.

14. The device according to claim 12, wherein the oxygen sensor comprises:
    a fluorophore,
    a light source for illuminating the fluorophore, and
    a detector for detecting fluorescence from the fluorophore.

15. The device according to claim 14, wherein oxygen quenches fluorescence from the fluorophore.

16. The device according to claim 14, further comprising a means for determining a concentration of oxygen in the interior from the detected fluorescence.

17. The device according to claim 14, wherein the oxygen sensor determines a concentration of oxygen in the interior from the detected fluorescence.

18. The device according to claim 1, wherein the substance is selected from the group consisting of: oxygen, carbon dioxide, water vapor, nitrogen, carbon monoxide, helium, hydrogen, ammonia, nitrogen oxides (NOx), sulfur oxides, hydrogen sulfide, hydrogen chloride, and aroma compounds.

19. The device according to claim 1, further comprising a means for mechanically agitating the interior.

20. The device according to claim 1, wherein the one or more walls comprise a top section and bottom section, wherein the top section and bottom section are sealably connected.

21. The device according to claim 20, wherein the top section comprises the aperture.

22. The device according to claim 1, wherein the one or more walls are rigid.

23. The device according to claim 1, wherein the one or more walls are flexible.

24. The device according to claim 1, wherein the substance is a gas.

25. A method for measuring the transmission rate of a substance through a sample, comprising:
    providing a chamber having one or more walls that define an interior and an exterior, wherein the one or more walls have an aperture therethrough such that the interior communicates with the exterior through the aperture;
    positioning a sample proximate the aperture such that the exterior and the interior are separated by the sample, wherein a first side of the sample is in contact with the exterior and a second side of the sample is in contact with the interior;
    exposing the first side of the sample to a substance;
    positioning a portion of a probe in contact with the interior, wherein the substance in the interior is detected by the probe, wherein the probe does not consume the substance during detection; and
    determining the transmission rate of the substance through the sample based on the detected substance.

26. The method according to claim 25, wherein the probe comprises a fluorophore, wherein the fluorophore is in contact with the interior.

27. The method according to claim 25, wherein the transmission rate is based on the time dependence of the detected substance.

28. The method according to claim 25, wherein the substance is a gas.

29. The method according to claim 28, wherein the gas is oxygen.

30. The method according to claim 29, wherein the probe detects oxygen, wherein the probe does not consume oxygen during detection.

31. The method according to claim 30, further comprising a port for insertion of the oxygen sensor into the interior.

32. The method according to claim 30, wherein the probe comprises:
a fluorophore,
a light source for illuminating the fluorophore, and
a detector for detecting fluorescence from the fluorophore.

33. The method according to claim 32, wherein oxygen quenches fluorescence from the fluorophore.

34. The method according to claim 32, further comprising determining a concentration of oxygen in the interior from the detected fluorescence.

35. The method according to claim 32, further comprising:
transmitting at pre-determined intervals information detected by the probe pertaining to the level of fluorescent energy to a spectrophotometer via the optical fiber;
calculating at each interval the partial pressure of oxygen present on the second side of the material utilizing the transmitted information; and
calculating at each interval the oxygen transmission rate of the material.

36. The method according to claim 35, further comprising creating a visual representation of the change in oxygen transmission rate of the sample over time.

37. The method according to claim 25, further comprising:
providing an inlet port for passing a purge gas or mixture from the exterior to the interior;
providing an outlet port for allowing gasses to pass from the interior to the exterior; and
inputting the purge gas or mixture through the inlet port, such that gasses in the interior are purged from the interior to the exterior through the outlet port.

38. The method according to claim 25, wherein the sample is perforated.

39. The method according to claim 38, wherein the sample comprises a permeable material.

40. The method according to claim 38, wherein the sample comprises a non-permeable material.

41. The method according to claim 25, wherein the sample is non-perforated.

42. The method according to claim 25, wherein the sample comprises a permeable material.

43. The method according to claim 25, wherein the sample comprises a non-permeable material.

44. The method according to claim 37, wherein the purge gas or mixture is a purge gas.

45. The method according to claim 44, wherein the purge gas is nitrogen.

46. The method according to claim 25, wherein the substance is selected from the group consisting of: oxygen, carbon dioxide, water vapor, nitrogen, carbon monoxide, helium, hydrogen, ammonia, nitrogen oxides (NOx), sulfur oxides, hydrogen sulfide, hydrogen chloride, and aroma compounds.

47. The method according to claim 25, further comprising mechanically agitating the interior.

48. The method according to claim 25, wherein the one or more walls comprise a top section and bottom section, wherein the top section and bottom section are sealably connected.

49. The method according to claim 48, wherein the top section comprises the aperture.

50. The method according to claim 25, wherein the one or more walls are rigid.

51. The method according to claim 25, wherein the one or more walls are flexible.

52. A device for measuring the transmission rate of a substance through a sample, comprising:
a chamber having one or more walls that define an interior and an exterior, wherein the one or more walls have an aperture therethrough such that the interior communicates with the exterior through the aperture,
a means for positioning a sample proximate the aperture such that the exterior and the interior are separated by the sample; and
a probe, wherein at least a portion of the probe is in contact with the interior such that the probe can detect a substance in the interior, wherein the probe does not consume the substance during detection.

* * * * *

UNITED STATES PATENT AND TRADEMARK OFFICE
CERTIFICATE OF CORRECTION

PATENT NO. : 8,567,236 B2
APPLICATION NO. : 12/335230
DATED : October 29, 2013
INVENTOR(S) : Bruce A. Welt and Ayman Abdellatief Page 1 of 1

It is certified that error appears in the above-identified patent and that said Letters Patent is hereby corrected as shown below:

In the Specification

Column 8,
Lines 36-38,

" $\ln\left[\dfrac{p_{O_2}^{ambient} - p_{O_2}^t}{p_{O_2}^{ambient} - p_{O_2}^0}\right] = \dfrac{-RT}{V_{total}} \cdot \dfrac{\overline{P}_{O_2} A}{l} \cdot t$ (5) "

should read

-- $\ln\left[\dfrac{\left(p_{O_2}^{ambient} - p_{O_2}^t\right)}{\left(p_{O_2}^{ambient} - p_{O_2}^0\right)}\right] = \dfrac{-RT}{V_{total}} \cdot \dfrac{\overline{P}_{O_2} A}{l} \cdot t$ (5) --.

Lines 43-45,

" $\ln\left[\dfrac{p_{O_2}^{ambient} - p_{O_2}^t}{p_{O_2}^{ambient} - p_{O_2}^o}\right]$ " should read -- $\ln\left[\dfrac{\left(p_{O_2}^{ambient} - p_{O_2}^t\right)}{\left(p_{O_2}^{ambient} - p_{O_2}^o\right)}\right]$ --.

Lines 62-64,

" $OTR = \dfrac{\overline{P}_{O_2}}{l} \cdot \left(p_{O_2}^{Air} - p_{O_2}^t\right)$ (7) "

should read

-- $OTR = \dfrac{\overline{P}_{O_2}}{l}\left(p_{O_2}^{ambient} - p_{O_2}^t\right)$ (7) --.

Signed and Sealed this
Twenty-second Day of July, 2014

Michelle K. Lee
*Deputy Director of the United States Patent and Trademark Office*